United States Patent [19]

Landucci et al.

[11] Patent Number: 5,308,626
[45] Date of Patent: May 3, 1994

[54] LYMPHOKINE ACTIVATED EFFECTOR CELLS FOR ANTIBODY-DEPENDENT CELLULAR CYTOTOXICITY (ADCC) TREATMENT OF CANCER AND OTHER DISEASES

[75] Inventors: Gary R. Landucci, 216 Saybrook Ct., Costa Mesa, Calif. 92627; Toni N. Mariani, 1924 E. River Ter., Minneapolis, Minn. 55414

[73] Assignees: Toni N. Mariani, Minneapolis, Minn.; Gary R. Landucci, Costa Mesa, Calif.

[21] Appl. No.: 808,958

[22] Filed: Dec. 13, 1991

Related U.S. Application Data

[63] Continuation of Ser. No. 355,148, May 16, 1989, abandoned, which is a continuation of Ser. No. 50,292, Apr. 27, 1987, abandoned, which is a continuation-in-part of Ser. No. 750,091, Jun. 28, 1985, abandoned.

[51] Int. Cl.$^5$ .................. A61K 45/05; A61K 39/395; A61K 37/66; A61K 35/14
[52] U.S. Cl. .................. 424/93 V; 424/85.1; 424/85.2; 424/85.4; 424/85.8; 435/70.4; 435/70.5; 435/240.2
[58] Field of Search .............. 435/70.3, 240.2; 424/85.8, 93, 93 V, 85.1, 534; 530/388.2, 388.7, 388.7 S, 388.8

[56] References Cited

U.S. PATENT DOCUMENTS 4,596,774  6/1987  Chang et al. .................. 435/6 X
4,690,915  9/1987  Rosenberg .................. 530/351
4,844,893  7/1989  Honsik et al. .................. 424/85.8

OTHER PUBLICATIONS

Moretta, L., et al. (1981) J. Exp. Med. 154:569-74.
Fabricius, H.-A. et al. (1979) Immunobiol. 156:364-71.
Fuson, E. W. et al. (1978) J. Immunol. 120:1726-32.
Guyre, P. M. et al. (1983) J. Clin. Invest. 72:393-97.
Fridman, W. H. et al (1980) J. Immunol. 124:2436-41.
Jones et al. (1980) J. Immunol. 125:926-33.
Journal Biological Response Modifier, 9, 1990, pp. 15-23 Riccardi et al.

Nio et al, Anticancer Research 10, 1990, pp. 441-446.
Plate et al, Annals of the New York Academy of Science vol. 532, 1988, pp. 149-157.
Issekutz, J Immunol 144, 1990, pp. 2140-2146.
J. W. Greiner, et al, "Enhanced Expression of Surface Tumor-associated Antigens on Human Breast and Colon Tumor Cells after Recombinant Human Leukocyte α-Interferon Treatment," Cancer Res., vol. 44, (1984), pp. 3208-3214.
K. Imai, et al, "Differential Effect of Interferon on the Expression of Tumor-associated Antigens and Histocompatibility Antigens on Human Melanoma Cells: Relationship to Susceptibility to Immune Lysis Mediated by Monoclonal Antibodies," J. Immunol., vol. 127 (1981), pp. 505-509.
E. B. Walker, et al, "Murine Gamma Interferon Activates the Release of a Macrophage-derived Ia-Inducing Factor that Transfers Ia Inductive Capacity," J. Exp. Med., vol. 159 (1984), pp. 1532-1547.
B. L. Cohen, et al, "Suppression by Alpha-Fetoprotein of Murine Natural Killer Cell Activity Stimulated in Vitro and in Vivo by Interferon and Interleukin 2," Scand. J. Immunol., vol. 23 (1986), pp. 211-223; Chemical Abstract, vol. 104 (1986).

(List continued on next page.)

Primary Examiner—Robert J. Hill, Jr.
Assistant Examiner—David L. Fitzgerald
Attorney, Agent, or Firm—Fredrikson & Byron

[57] ABSTRACT

This invention relates to processes and compositions for the immunotherapeutic treatment of cancer and non-malignant tumors. More particularly, this invention relates to processes and compositions for enhancing the body's immune response by increasing the cytotoxic activity of cells which mediate antibody dependent cellular cytotoxicity. Cells which are characterized by increased cytotoxic activity, as a result of the process of this invention, are useful in methods and compositions for the treatment of various types of cancer and non-malignant tumors.

21 Claims, No Drawings

OTHER PUBLICATIONS

M. G. Baines, et al, "Involvement of Transferrin and Transferrin Receptors in Human Natural Killer Effector:Target Interaction," *Immunol. Lett.* 7(1), pp. 51-55 (1983), Abst. No. 211018y (Chem. Abst., vol. 99, issued 1983.

E. Diener, et al, "Specific Immunosuppression by Immunotoxins Containing Daunomycin," *Science*, vol. 231 (1986), pp. 148-150.

J. C. Roder, et al, "Target-Effector Interaction in the Human and Murine Natural Killer System," *J. Exp. Med.*, vol. 150 (1979), pp. 471-481.

J. A. Werkmeister, et al, "Identification of a Structure on Human Melanoma Cells Recognized by CTL Exhibiting Anomalous Killer Cell Function," *J. Immunol.*, vol. 135 (1985), pp. 689-695.

D. Wallach, et al, "Preferential Effect of y Interferon on the Synthesis of HLA Antigens and their mRNAs in Human Cells," *Nature*, vol. 299 (1982), pp. 833-836.

Lanier et al *J Immunol* 134, 1985, pp. 794-801.

Shaw et al, Cell. Immunol 1985, 91, pp. 193-200.

Phillips et al J Exp Medicine 1985, pp. 1461-1482 vol. 161.

Nair et al *J Immunol* 129, 1982, pp. 2511-2518.

Burns et al, *J Immunol* 133, 1984, pp. 1656-1663.

Cheever et al; *J Biol Response Modifier* 3, 1984, pp. 113-127.

Kedou et al, J Biol Response Modifier 3, 1984, pp. 517-526.

Merluzzi et al, J Biol Response Modifier 3, 1984, pp. 468-474.

Guimar et al *J Exp Med* 155, 1982, pp. 1823-1841.

Lotz et al *Carrier Res* 41, 1981, pp. 4420-4425.

Lotz et al *J Biol Response Modifier* 3, 1984, pp. 475-482.

Imai et al Scand. *J Immunol* 14, 1981, pp. 369-377.

Schultz et al *PNAS* 80, 1983, pp. 5407-5411.

Gore et al, *B J Cancer* 48, 1983, pp. 877-879.

Simone et al, *Nature* 297, 1982, pp. 234-236.

Jones et al *J Immunol*, vol. 125, 1980, pp. 926-933.

Kosugi et al, *Jpn J Cancer Chemother.* 11(8) 1984, pp. 1527-1535.

Bakais et al, *J Clin Lab Immunol* 1984, pp. 77-84, vol. 15.

Fukui et al, *Proc 14th Internal Congress of Chemotherapy* vol. 2 1985 pp. 971-972.

Mule et al, *Science* 225; 1984, pp. 1487-1489.

Hefeneider et al, *J Immunol* 130(1) 1983, pp. 222-227.

Chang et al, *J. Biol Resp Modifiers* 3, 1984, pp. 561-572.

LYMPHOKINE ACTIVATED EFFECTOR CELLS FOR ANTIBODY-DEPENDENT CELLULAR CYTOTOXICITY (ADCC) TREATMENT OF CANCER AND OTHER DISEASES

This is a continuation of application Ser. No. 355,148, filed May 16, 1989 (now abandoned), which is a continuation of application Ser. No. 050,292, filed Apr. 27, 1987 (now abandoned), which is a continuation-in-part of application Ser. No. 750,091, filed Jun. 28, 1985 (now abandoned).

TECHNICAL FIELD OF INVENTION

This invention relates to the immunotherapeutic treatment of cancer and non-malignant tumors. More particularly, this invention relates to a process for enhancing the body's immune response by increasing the cytotoxic activity of cells which mediate antibody dependent cellular cytotoxicity. Cells which are characterized by increased cytotoxic activity, as a result of the process of this invention, are useful in methods and compositions for the treatment of various types of cancer and non-malignant tumors.

BACKGROUND ART

The transformation of normal cells within the body into cancerous and non-malignant neoplasms may be induced by viral infections, chemical carcinogens, radiation, physical agents or spontaneous tumorigenic growth. As a result of such transformation, normal cell surface antigen expression may be altered. New antigens—tumor specific antigens or antigens characteristic of premature cell types—or antigen expression pattern changes may be demonstrated on many tumor types. These antigenic changes are targets for the body's immune response.

In some instances, the extent or rate of cell transformation may exceed the capabilities of the body's immune response. Alternatively, the immune response may itself be ineffective or deficient. Supplemental methods have, therefore, been used in the treatment of transformed cells. These methods include non-surgical treatments, such as chemotherapy and radiation, and surgical treatments. Typically, these treatments are characterized by a range of undesirable side effects. Non-surgical treatments having immunosuppressant effects may increase the patient's susceptibility to secondary infections. Surgical treatments to excise transformed cells involve risks attendant with invasive procedures and may not effectively remove or eliminate the entire transformed cell population.

An alternative method of treatment for cancers and non-malignant tumors has involved the use of monoclonal antibodies to tumor specific antigens on the surface of transformed cells. The effectiveness of such treatments, typically involving murine monoclonal antibodies, is often limited by a variety of factors. For example, human patients treated with murine monoclonal antibodies may develop an anti-murine immunoglobulin response which severely reduces the effectiveness of further administration of murine monoclonal antibodies (G. E. Goodman et al., "Pilot Trial of Murine Monoclonal Antibodies In Patients With Advanced Melanoma", *Journal Of Clinical Oncology*, 3, pp. 340-51 (1985)). Other reported side effects of monoclonal antibody treatments include anaphylaxis, fever and chills.

Monoclonal antibodies are also ineffective in the treatment of those tumor specific surface antigens which modulate upon exposure to specific antibodies. Such antigens include, for example, the common acute lymphocytic leukemia antigen ("CALLA"), which appears on the surface of transformed cells of a majority of patients suffering from acute lymphocytic leukemia (J. Ritz et al., "Serotherapy Of Acute Lymphoblastic Leukemia With Monoclonal Antibody", *Blood*, 58, pp. 141-52 (1981)). When the CALLA antigen on the surface of a tumor cell is exposed to its specific antibody, the antigen migrates and the cell may internalize the antigen and antibody, preventing recognition of the tumor cell as a target by immune response effector cells such as leukocytes, lymphocytes, macrophages, killer ("K") cells or natural killer ("NK") cells.

In view of the disadvantages of such supplemental treatments, various therapies have been directed to augmenting the body's natural immune response to transformed cells. It is known that in the presence of antibodies, certain effector cells, such as lymphoid cells having surface bound receptors for the Fc regions of antibodies, mediate an antibody dependent cellular cytoxicity ("ADCC") reaction against target cells. By means of ADCC, these effector cells exert cytolytic activity against such target cells.

Two types of ADCC reactions have been demonstrated in vitro. In classical ADCC reactions, effector cells attach to antibody-coated target cells and subsequently cause cytolysis of the target cells (A. H. Greenberg et al., "Characteristics Of The Effector Cells Mediating Cytotoxicity Against Antibody-Coated Target Cells. I., *Immunology*, 21, p. 719 (1975)). This attachment between effector and target cell results from the interaction of the Fc region of the antibody coating the target cell and the Fc receptor of the effector cell. One disadvantage of this type of ADCC reaction is that it may be hampered by circulating antigen-antibody complexes, often associated with various diseases, which compete with the target-cell bound antibody for the Fc receptors of the effector cells (I. C. M. MacLennan, "Competition For Receptors For Immunoglobulin On Cytotoxic Lymphocytes", *Clin. Exp. Immunol.*, 10, p. 275 (1972)). Due to this drawback of classical ADCC, a second type of ADCC reaction—antibody-directed ADCC—has been proposed. In antibody-directed ADCC, the target-specific antibody is first attached to the effector cell and the resulting complex is then "directed", via the antibody, to its specific antigen on the target cell surface. Advantageously, antibody-directed ADCC may not be affected by the presence of antigen-antibody complexes circulating in the host system.

The interaction between antibodies and effector cells via Fc region/Fc receptor attachment is normally weak. And, in some instances, antibodies do not remain associated with effector cells for a period of time sufficient to permit lysis of target cells. In view of this potential problem, antibodies have been attached to the effector cells using pretreatment with polyethylene glycol and a mixture of phthalate oils (J. F. Jones and D. M. Segal, "Antibody-Dependent Cell Mediated Cytolysis (ADCC) With Antibody-Coated Effectors: New Methods For Enhancing Antibody Binding And Cytolysis", *J. Immunol.*, 125, pp. 926-33 (1980)). The applicability of this method for in vivo treatments, however, may be diminished by the toxic effects that any polyethylene glycol and phthalate oil residues on the antibody-effector cell complex may have on the body.

Alternatively, a method has been proposed for enhancing antibody-directed ADCC by adjuvant chemotherapy with cytotoxic drugs (I. R. Mackay et al., "Effect On Natural Killer And Antibody-Dependent Cellular Cytotoxicity Of Adjuvant Cytotoxic Chemotherapy Including Melphalan In Breast Cancer", *Cancer Immunol. Immunother.*, 16, pp. 98–100 (1983)). Such a method, however, risks undesirable side effects resulting from the use of cytotoxic drugs.

Therefore, conventional means for treating cancer and non-malignant tumors by either supplementing or enhancing the body's immune response are characterized by various disadvantages. The need, thus, exists for an effective process and composition which avoid those disadvantages while providing effective treatment for cancers and non-malignant tumors.

DISCLOSURE OF THE INVENTION

The present invention solves the problems referred to above by providing a process for enhancing the immune response of the body to cancers and non-malignant tumors by activating effector cells which mediate antibody dependent cellular cytotoxicity ("ADCC") to increase their cytotoxic activity beyond normal levels to between at least 1.25 and 125 times that of effector cells in their natural state. Effector cells which are characterized by such increased cytotoxic activity, as a result of this process, may then advantageously be used in methods and compositions of this invention for the immunotherapeutic treatment of cancer and non-malignant tumors. In addition, one preferred embodiment of this invention provides a process for more efficiently directing these activated effector cells to target cells by the attachment of target-specific antibodies to the Fc receptors on the surface of the activated effector cells. It also provides compositions characterized by such specific antibody effector cell complexes.

The processes and compositions of this invention may be used to cause regression, remission or prevention of transformed cell growth, to prevent metastatic growth throughout the body or to increase immunity of the host upon rechallenge with the disease-causing agent. Advantageously, the processes and compositions of this invention enhance the body's natural immune response of cell-mediated immunity via ADCC and, therefore, do not incur the variety of side effects which characterize conventional cancer and tumor treatments.

DETAILED DESCRIPTION OF THE INVENTION

In a first embodiment, this invention provides a process for pre-selection of Fc receptor positive cells from a pool of bulk lymphoid cells obtained by density gradient centrifugation techniques or other methods of leukocyte separation.

This invention also relates to a process for treating effector cells which mediate antibody dependent cellular cytotoxicity to increase their cytotoxic activity beyond normal levels. One embodiment of this process comprises the steps of recovering effector cells from a donor and activating the cells in vitro to increase their antibody dependent cellular cytotoxic activity. This invention also relates to cells activated by that process.

This invention also relates to a process and composition for treating cancer and non-malignant tumors. Generally, this process comprises the step re-introducing effector cells activated by the processes of this invention into the donor or transferring the activated cells to a recipient. According to an alternate and preferred embodiment of this invention, antibodies which are specific for the cancer or non-malignant tumor to be treated are first attached to the activated effector cells before they are re-introduced to the donor or transferred to the recipient.

Treatment of effector cells according to the processes of this invention activates them by increasing their antibody dependent cytotoxic activity against target cells. This increase in antibody dependent cytotoxic activity ranges between at least about 1.25 and 25 times, and in some instances between at least about 1.25 and 125 times, that of non-treated effector cells in their natural state.

Without being bound by theory, we believe that this increased antibody dependent cytotoxic activity is due to increased Fc receptor expression on the surfaces of effector cells activated by the processes of this invention. Specifically, we believe that our activated cells are better able to mediate antibody dependent cellular cytotoxicity because more Fc receptors are present on effector cells after treatment according to this invention, and therefore tumor-specific antibodies (coating the target cells or exogenous to them) having an Fc region are more likely to attach to the effector cells in an effective way, i.e. via the Fc region of the antibody to an Fc receptor on the effector cell, so that the attachment will be maintained and ADCC ensured.

In addition, since more Fc receptors are present on the activated effector cells, a greater number of target-specific antibodies may attach to each effector cell. The increased density of antibodies per effector cell not only permits a greater number of antibodies to be present on or reach the target transformed cell for each effector, but also increases the ability of an effector to recognize or locate the target cell and, thus, to mediate ADCC. The overall result of these effects on treated effector cells is the enhancement of the body's immune response against target cells. Such enhancement is particularly advantageous to the treatment of diseases which cause a decrease in or absence of effector cells in the patient's immune system.

Diseases which may be treated by the processes and compositions of this invention are those characterized by an undesirable proliferation of target cells to which antibodies may be specifically directed. Such diseases include malignant and non-malignant solid or fluid tumors, carcinomas, myelomas, sarcomas, leukemias and lymphomas. In addition, effector cells activated according to the processes of this invention may be administered prophylactically for the prevention of cancer and non-malignant tumors.

It should also be understood that effector cells activated according to this invention may be used, preferably with an appropriate antibody, to exert enhanced ADCC activity against any type of target cells. Effector cells activated according to the processes of this invention demonstrated increased cytotoxic activity in ADCC and anti-tumor cell proliferation assays against target human cells such as, for example, those derived from the K562 tumor cell line, a human myelogenous leukemia (H. Pross and M. Baines, "Spontaneous Human Lymphocyte-Mediated Cytoxicity Against Tumour Target Cells I. The Effect of Malignant Disease", *Intl. J. Cancer*, 18, pp. 593–604 (1976)); the Nalm-6 leukemia cell line (gift of Dr. Tucker LeBien, University of Minnesota); fresh samples of acute lymphoblastic leukemia cells and fresh preparations of chronic myelogenous leukemia cells. Activated effector cells also demonstrated increased cytotoxic activity against murine target cells such as, for example, Zbtu murine T-cell lymphoma cells; EL-4 murine cells (ATCC Tib-39) P815 murine cells (ATCC Tib-64) and Yac murine cells (R. Kiessling et al., "Genetic Variation Of In Vitro Cytolytic Activity And In Vivo Rejection Potential Of Non-Immunized Semi-Syngeneic Mice Against A Mouse Lymphoma Line", *Intl. J. Cancer*, 15, pp. 933–40 (1975)).

The processes and compositions of this invention may be used to treat any mammal, including humans. Preferably, the source of the effector cell is the patient to be treated. However, effector-mediated ADCC is neither patient-specific nor species-specific. Effector cells derived from one patient or species and activated according to the processes of this invention may, therefore, be used in another patient or species to exert cytotoxic activity against target cells. The use of activated effector cells donated from another patient or species may be necessitated for recipients having depressed levels of effector cells. Although such treatment with donated effector cells will ultimately lead to rejection of the cells by the recipient, some degree of antibody dependent cellular cytotoxic activity by the activated effector cells will normally take place before those cells are rejected and that activity may be sufficient to affect the course of the disease to be treated.

Effector Cells

Effector cells which may be activated by the processes of this invention include any type of cytotoxic cell having a surface receptor for the Fc region of an antibody and which can mediate ADCC. Such effector cells include, for example, leukocytes, such as lymphocytes, monocytes, K cells and NK cells.

Such cells may be isolated in a wide variety of ways including isolation directly from syngeneic donors and from 1 to 7 day cultures of such cells. For example, effector cells may be isolated by a process in which spleens were removed from mice, minced and washed in sterile balanced saline solution and the leukocytes isolated by centrifugation through lymphocyte separation medium (LYMPHO-PAQUE, Accurate Chemical and Scientific Corporation, Westbury, N.Y.) to a final concentration of about $5 \times 10^7$ cells/ml.

Human effector cells may be isolated, for example, from peripheral blood according to a modification of the procedure described by A. Böyum, "Lymphocytes. Isolation, Fractionation and Characterization", J. B. Natvig et al. (Ed.), *Scand. J. Immunol.*, 5: Suppl. 5, pp. 9–15 (1976). In some cases, the leukocyte population may be further sorted by gradient centrifugation (Ficoll-Hypaque density gradient, Pharmacia Fine Chemicals, Piscataway, N.J.) to separate out the mononuclear white cells. The mononuclear leukocytes obtained at this point may then be either used as a source for effector cells or further treated using standard techniques to sort out more reactive cells or only those cells having Fc receptors. Such techniques include separation or enrichment techniques using monoclonal antibodies, sorting with FACS IV (fluorescence activated cell sorter, Becton Dickinson, FACS Division, Sunnyvale, Calif.) or adherence techniques.

For example, various antibodies may be used to obtain the effector cells to be treated according to the processes of this invention. Antibodies used to identify, label, characterize, sort, separate, enrich and/or deplete effector cells treated in the processes of this invention included, for example, the following:

(1) HNK-1, Leu-7 (Becton Dickinson, Mountain View, Calif.—Catalog No. 73-90)
(2) Leu-11-a (Becton Dickinson—Catalog No. 75-23)
(3) Leu-11-b (Becton Dickinson—Catalog No. 75-30)
(4) Leu-11-c (Becton Dickinson—Catalog No. 76-17)
(5) Anti-IL2-Receptor (Becton Dickinson—Catalog No. 76-40)
(6) Anti-Human Fc Receptor (New England Nuclear, Boston, Mass.—Catalog No. Nei033)
(7) Goat Anti-Mouse IgG Fc Fragment F(ab')$_2$ (Jackson Immuno-Research Labs, Avondale, Pa.—Catalog No. 115-0646)
(8) Rabbit Anti-Goat IgG Fc Fragment F(ab')$_2$ (Jackson Immuno-Research Labs—Catalog No. 305-0608)
(9) Rabbit Antigoat IgG (Cappel, Malvern, Pa.—Catalog No. 0612-3151).
(10) Mouse IgG1 (Catalog No. 9041, Litton Bionetics Inc., Kensington, Md.)
(11) MOPC 104E, a purified mouse myeloma protein (Catalog Nol 8402-29, Litton Bionetics, Inc.).

For example, mononuclear leukocytes may be labelled with Anti-Leu-11a, Anti-Leu-11b or Anti-Leu-11c antibodies (Becton Dickinson) and only those cells labelled with antibodies may be sorted by positive selection. Alternatively, since cells that have Fc receptors fall into the size range of 7 $\mu$m-25 $\mu$m diameter, an elutriator centrifuge [Beckman Instruments] which sorts cells based on size may be used.

As an alternative to the above procedures for obtaining effector cells from human donors, it is possible to utilize a leukaphoresis technique using, for example, a Fenwal CS-3000 (Fenwal Labs, Deerfield, Ill.) or a Haemonetics Model 30 leukaphoresis machine (Haemonetics Corp., Braintree, Mass.) [T. Loftus et al., "Leukophoresis: Increasing The Granulocyte Yield With the Fenwal CS 3000", *J. Clin. Apheresis*, 1, pp. 109–14 (1983) and H. Braine et al., "Peripheral Blood Lymphocyte Proliferative Response In Vitro And Serum Immunoglobulins In Regular Hemaphoresis Donors", *J. Clin. Apheresis*, 2, pp. 213–18 ((1985)]. Leukophoresis permits leukocytes to be obtained from circulating peripheral blood via a centrifuge placed in line with a patient access line. The leukocytes are harvested and red cells are returned to the patient. This technique advantageously permits the collection of more white cells and, therefore, more effector cells having Fc receptors, than those obtained from one unit of blood.

After they are obtained from the patient or donor, effector cells are placed in a balanced salt solution medium, such as Hanks balanced salt solution or tissue culture medium such as RPMI-1640 supplemented with heat inactivated 5% fetal calf serum, 5% ULTROSER G or 5% autologous serum which may be supplemented with an antibiotic such as, for example, Gentamicin (5 $\mu$g/ml), Penicillin (10 units/ml), Streptomycin (10 $\mu$g/ml), or mixtures thereof, and maintained in a refrigerator at 4° C. If the effectors are to be maintained in vitro for over 24 hours, they are placed in a medium which also contains essential nutrients for cell viability. Preferably, they are stored frozen by quickly freezing them to −70° C.

Activation of effector cells according to this invention may be carried out by treating the cells, in vitro, with lymphokines, allogeneic or zenogeneic serum, or mixtures thereof. The lymphokines used may be those purified from natural sources using conventional techniques or those produced by recombinant techniques. The preferred lymphokines for use in this invention are gamma interferon ("γ-IFN") and interleukin-2 ("IL-2"), and these may be used alone, in combination, or in series, for the activation of effector cells. The preferred dosage of γ-IFN is about 600 units/ml, with an approximate effective range of between about 200 and 2500 units/ml. The preferred dosage of IL-2 is about 750 units/ml, with an approximate effective range of between about 30 and 2000 units/ml. Serial combination treatment with these two lymphokines is most preferably carried out by γ-IFN treatment first, followed by IL-2 treatment, at the dosages indicated for the individual treatments.

According to this invention, effector cells are usually treated in vitro with the lymphokine, allogeneic or xenogeneic serum or mixtures thereof and incubated at 37° C. in a 5% $CO_2$ atmosphere or refrigerated at 4° C. for a period of time sufficient to permit the cells to be activated so that their antibody dependent cellular cytotoxicity is increased beyond normal levels, as determined by serial sampling for verification of activated function. More specifically, effector cells in suspension preferably having a range of $10^5$ to $10^7$ effector cells per ml of media are treated with the lymphokine, allogeneic or xenogeneic serum, or mixtures thereof, for preferably between about 1 and 7 days, most preferably between about 3 and 4 days.

Effector cells may be stored frozen after being activated and before being administered to the patient. Alternatively, effector cells may be partially activated, stored frozen, thawed and further activated before use. For example, activated effector cells may be placed in tissue culture medium supplemented with fetal calf serum, normal human serum, or serum substitutes, such as ULTROSER G, and dimethyl sulfoxide ("DMSO") and frozen as quickly as possible, to at least −70° C., using a controlled rate cell freezer or any conventional method for freezing. After storage, frozen activated effector cells may be thawed as quickly as possible without raising the temperature of the cells above 37° C.

Preferably in the processes and compositions of this invention, antibodies are used with the activated effector cells to mediate an enhanced ADCC effect against target cells and to indicate the level of effector cell activation achieved. Such antibodies are those of the IgG class, preferably IgG2 antibodies, which have Fc regions and which primarily recognize antigens that are either specific to a particular cancer or non-malignant tumor or present in higher densities on cells of cancer or non-malignant tumors than on normal cells.

Examples of such antibodies include the following:
(1) GAGPA-Goat anti-Gross passage A virus (National Institutes Of Health, Bethesda, Md.)
(2) PAGPA-Pig anti-Gross passage A virus (National Institute Of Health, Bethesda, Md.)
(3) Anti-CALLA (Becton Dickinson, Mountain View, Calif.—Catalog No. 7500)
(4) J-5 Anti-CALLA (Coulter Immunology, Florida—Catalog No. 6602143)
(5) BA3 Anti-CALLA (Hybritech, Inc., San Diego, Calif.—Catalog No. 0672)
(6) ANTI-HpCA-1 (Becton Dickinson—Catalog No. 7660)
(7) Rabbit Anti-Nalm 6 (a polyclonal antibody raised by hyperimmunizing a New Zealand female rabbit by intravenous injection of $1 \times 10^7$ Nalm-6 cells once a week for five weeks).

According to one preferred embodiment of this invention, the antibodies, which are specific for the target transformed cells, are attached to the activated effector cells before those cells are administered to the patient. This attachment may be carried out by incubating the activated effector cells in vitro with high concentrations of single or pooled monoclonal or polyclonal antibodies. For example, this attachment may be carried out by contacting the activated effector cells with antibodies, in a ratio of about $10^7$ cells per 2 mg of antibody and maintaining the mixture at room temperature or at 37° C. or refrigerating the mixture at 4° C. for between about 1 and 72 hours. Activated effector cells with antibodies attached are termed "armed" effector cells hereinafter.

For example, to attach an antibody to buffy coat leukocytes which have been activated according to the processes of this invention, the leukocytes are first washed three times in RPMI-1640 by centrifugation in a Beckman TJ-6 centrifuge equipped with a TH-4 rotor at 1200 rpm for 5 minutes. The multistep washing procedure removes loosely bound cytophilic immunoglobulins and may increase the availability of Fc receptors for binding of the desired antibodies. The effector cells may then be further purified by centrifugation on a density gradient medium such as Ficoll-Hypaque (Litton Bionetics, Bethesda, Md.). The collected leukocyte interface may then be resuspended in RPMI-1640 medium containing antibodies at concentrations of at least about $5 \times 10^7$ effector cells per 0.5 to 2.0 mg antibodies and incubated at room temperature or 37° C. or refrigerated at 4° C. for between about 1 and 72 hours with gentle rocking. The effector cells may then be allowed to sediment through gelatin plasma substitutes, such as PLASMAGEL (HIT Corporation, Buffalo, N.Y.) or by centrifugation on density gradient medium such as Ficoll-Hypaque, to "fix" the antibody attachment to the effector cells prior to administration to the patient. Effector cells attached to target-specific antibodies may then be administered to the patient as described below.

Patients with cancer or non-malignant tumors may be treated by the administration of a therapeutically or oncologically effective amount of effector cells which have been activated according to the processes of this invention. These activated effector cells also preferably have antibodies specific for the target cells attached to them before administration, as described supra. The activated effector cells may be administered in liquid dosage forms by means of intravenous injection or infusion. Injectable/infusable solutions of activated effector cells may also include conventional pharmaceutically acceptable carriers such as sterile saline solution.

The amount of activated effector cells administered at one time or over a series of treatments, will depend upon the volume and activity of the activated effector cells available for and present in the initial dose, the patient's health status, the severity and course of the cancer or non-malignant tumor and the judgment of the treating physician. Effective dosages may be in the range of between about $1 \times 10^6$ and $5 \times 10^{10}$ cells. The effectiveness of treatments may be assessed by analyzing samples of blood or bone marrow (in cases of leukemias and lymphomas) or by measuring rates of reduction on tumor load (in cases of tumorigenic diseases) at various post-treatment intervals.

When the treated effector cells are to be administered without antibodies attached, the patient may be pretreated with antibodies or other substances to increase the levels of circulating antibodies in the body, preferably tumor specific ones. For example, the patient may be treated by intravenous injection or infusion with a single monoclonal or polyclonal tumor-specific antibody or a pool of two or more tumor-specific monoclonal or polyclonal antibodies. Useful antibodies are immunoglobulin-G "IgG" class antibodies having demonstrable ADCC mediating potentials, as assessed by in vitro analyses, and which recognize tumor-specific antigens or antigens found preferentially or in greater densities on cancerous or non-malignant tumor cells.

In order that the invention described herein may be more fully understood, the following examples are set forth. It should be understood that these examples are for illustrative purposes only and are not to be construed as limiting this invention in any manner.

EXAMPLES

In the following examples, two assays were used to assess the cytotoxic activity and anti-tumor proliferation potentials of effector cells before and after being activated according to the processes of this invention. These assays were an ADCC $^{51}$chromium release assay and an anti-tumor cell proliferation assay.

ADCC $^{51}$Chromium Release Assay

The $^{51}$chromium release assay is a measure of effector cell cytotoxic activity. For the ADCC $^{51}$chromium release assay, we used a modification of the method described by R. Perlmann and G. Perlmann, "Contactual Lysis Of Antibody Coated Chicken Erythrocytes By Purified Lymphocytes", *Cell Immunol.*, 1, p. 300 (1970).

We labelled target cells with $^{51}$Cr (sodium chromate) [DuPont-New England Nuclear, catalog # NEZ-030S; 1 mCi/ml concentration] as follows. $2.5 \times 10^6$ or $5.0 \times 10^6$ target cells were pipetted into a $17 \times 100$ mm plastic centrifuge tube and incubated with, respectively, 0.05 ml $^{51}$Cr or 0.1 ml $^{51}$Cr for 75 minutes at 37° in a 5% $CO_2$ humidified atmosphere (Forma Scientific Water Jacketed Gas Processor Incubator—Model 3315, Forma, Marietta, Ohio). The tube remained loosely capped and was shaken once midway during the 75 minute incubation period. To wash the cells, we added 5 ml of a wash medium containing RPMI-1640 (Gibco Laboratories, Grand Island, N.Y.) supplemented with heat inactivated 5% fetal calf serum (Gibco Laboratories) and spun the tube in a Beckman TJ-6 centrifuge equipped with a TH-4 rotor (Beckman Instruments, Palo Alto, Calif.) at 1200 rpm for 5 min. We removed the supernatant and added 5.0 ml (for $2.5 \times 10^6$ labelled cells) or 10.0 ml (for $5.0 \times 10^6$ labelled cells) wash medium to give a final concentration of $5.0 \times 10^5$ labelled cells/ml. We then apportioned 1.0 ml of the labelled cells into 4 ml tubes and grouped them for treatment as follows.

The first group of target cells, which were not to be labelled with antibody, were washed 2 times with 1.5 ml wash medium and spun down for 5 min. at 1200 rpm. The supernatant was removed and the target cells were then resuspended in 1.0 ml wash medium to a concentration of $5 \times 10^5$ viable cells/ml. We then adjusted the cells to a final concentration of $5 \times 10^4$ viable cells/ml in wash medium.

The second group of target cells, which were to be labelled with antibody, were spun for 5 minutes at 1200 rpm. We removed the supernatant and resuspended the pelletized target cells in 0.10 to 0.25 ml of the appropriate antibody. The target cell/antibody mixture was incubated for 30 minutes, with shaking, at room temperature. We then added 1.5 ml wash medium to the mixture and spun the cells for 5 minutes at 1200 rpm. We removed the supernatant and repeated the washing step three times. We then resuspended the target cells in wash medium to provide a final concentration of $5 \times 10^4$ viable cells/ml.

We prepared the effector cells (activated by the processes of this invention or unactivated) as follows. We washed the effector cells in 10 ml of a medium containing RPMI-1640 and spun them down in a Beckman TJ-6 centrifuge equipped with a TH-4 rotor for 5 min at 1200 rpm. We removed the supernatant and resuspended the effector cells in wash medium to a final concentration of $7 \times 10^6$ viable effectors/ml for assays at an effector:target ratio of 140:1 and $2.3 \times 10^6$ viable effectors/ml for assays at an effector:target ratio of 47:1, i.e., so that 0.5 ml of effector cells were present for each target.

We plated the target cells and effector cells in a 96 well microtiter plate in triplicate (Costar Plastics, Cambridge, Mass.). Spontaneous wells were defined as those to which target cells and diluent were to be added. Maximum wells were defined as those to which target cells and detergent were to be added. Effector wells were those to which effector cells, target cells and, in some cases, diluent were to be added, and in which effector cell:target cell ratios may also be in the range of between about 140:1 and 1:1.

We pipetted 0.1 ml diluent, RPMI-1640 medium, into each spontaneous well and into each effector well having the highest effector:target ratios. No diluent was added to either the first three wells or the maximum wells of each target row. We then pipetted 0.15 ml of effector cells into the first three wells of each target row and made 1:3 serial dilutions of the effectors through the triplicates. To do this, we removed 0.05 ml of effector cells from each of the first wells and transferred them to each of the fourth wells using a pipette. We mixed the fourth wells, removed 0.05 ml of effector cells from each of the fourth wells and added them to each of the seventh wells. We mixed each of the seventh wells and removed 0.05 ml of their contents. We repeated this dilution procedure for each of two series of wells: 2, 5 and 8 and 3, 6 and 9. We then added 0.1 ml of target cells (concentration of $5 \times 10^4$ viable cells/ml) to the wells of each target row. Subsequently, we added 0.1 ml of detergent, TRITON X-100, 1% in RPMI-1640 medium, to those wells which contained target cells but no diluent, i.e., the maximum wells.

We then balanced the plates and spun them at 1000 rpm for 1 minute to effect cell to cell contact. The plates were then incubated at 37° C. for 4 hours in a humidified atmosphere of 5% $CO_2$ in air. At the end of 4 hours, we centrifuged the plates for 10 minutes at 2000 rpm. We then removed 0.1 ml of the supernatant from each well, while avoiding any pellet disturbance, and added it to a liquid scintillation counter mini vial (Beckman Instruments). We then added 1 ml scintillation cocktail (Beckman HP/b) to each tube, capped the tube and shook it. We placed each tube into a liquid scintillation counter (Beckman Instruments1, Model LS-3801) and began 1 minute counts to measure radioactivity.

The percent of specific target cell cytotoxicity was determined by averaging triplicate count per minute ("CPM") measurements of $^{51}$chromium according to the following formula:

$$\% \text{ lysis} = \frac{\text{experimental } cpm - \text{spontaneous } cpm}{\text{maximal } cpm - \text{spontaneous } cpm} \times 100$$

wherein:
experimental cpm = radioactivity released from target cells in the presence of effector cells
spontaneous cpm = radioactivity released from target cells in the absence of effector cells
maximal cpm = radioactivity released from target cells in the presence of detergent.

Anti-Tumor Cell Proliferation Assay

The anti-tumor cell proliferation assay is a measure of the ability of effector cells to inhibit proliferation of tumor cells in vitro by ADCC.

Target tumor cells were collected from tissue culture flasks, washed in RPMI-1640 and resuspended in growth medium to achieve a concentration of $1.25 \times 10^4$ viable cells/ml. Wells 7–36 of a 96 well u-bottom sterile microtiter plate (Costar Plastics) were plated with 80 ml of culture growth medium using a TITER-TEK multichannel pipettor (made for Flow Laboratories by Eflab Oy, Finland).

Effector cells (activated by the processes of this invention or unactivated) were washed with RPMI-1640 and adjusted to a concentration of $2.5 \times 10^6$ viable cells/ml. We plated effector cells in replicate wells of six to achieve six effector to target ratios: 200:1; 100:1; 50:1; 25:1; 13:1; 6:1, in a total of 36 wells. Wells 1–6 were each plated with 160 µl of effector cells from the $2.5 \times 10^6$ concentration. We removed 80 µl of effector cells from each of wells 7–12 and transferred them to, respectively, wells 13–18, and mixed them by repeat pipetting. This 1:2 dilution was repeated out to well #36. We then discarded 80 µl from wells 30–36. We added 20 µl of appropriate test antibody to each well of the experimental rows and 20 µl of culture medium to 36 control wells of effector cells ("Control No. 2"). Subsequently, we added 80 µl of target cells to each well of the experimental rows (the 36 Control No. 2 wells and the 36 control wells containing antibody only). Eighty µl of culture medium were added to 36 control wells containing effectors only ("Control No. 1").

We incubated the plates at 37° C. in humidified 5% $CO_2$ and air for a total time of 24 hours. After 20 hours of culture, 50 µl of $^3$H-thymidine (Dupont-New England Nuclear) from a concentration of 20 µCi/ml was added to all wells. Fifteen minutes prior to harvesting all wells, we added 15 µl of trypsin (Gibco Laboratories, New York) 1:250 concentration, to all wells to effect cell detachment from plastic. All wells were subsequently harvested onto filter disks, PHD No. 240-1 Glass Fiber Filter Strips (Cambridge Technology, Cambridge, Mass.) by automated cell harvesting with a PHD cell harvester (Cambridge Technology, Cambridge, Mass.). We placed dried filters into plastic minivials (Beckman Instruments) filled the vials with 2.0 ml of scintillation cocktail (HP/b, Beckman), shook them vigorously, and counted for beta in a liquid scintillation counter. Disintegrations per minute ("DPM") were calculated and six replicates were averaged ("$\bar{x}$"). Control wells of effectors and targets without antibody served as base for tumor proliferation. Percent inhibition as a measure of anti-proliferation was calculated according to the following formula:

$$\% \text{ inhibition} = \left(1 - \frac{\bar{x}DPM \text{ experimental} - \bar{x}DPM \text{ Control No. 1}}{\bar{x}DMP \text{ Control No. 2} - \bar{x}DMP \text{ Control No. 1}}\right) \times 100$$

When the anti-proliferation assay was conducted with "armed" effector cells, we calculated percent inhibition as a measure of antiproliferation according to the following formula:

$$\% \text{ inhibition} = \left(1 - \frac{\bar{x}DPM \text{ experimental} - \bar{x}DPM \text{ Control No. 3*}}{\bar{x}DPM \text{ Control No. 2} - \bar{x}DPM \text{ Control No. 1}}\right) \times 100$$

*"Control No. 3" represents the values obtained from cultures of "armed" effector cells without target cells.

For the purposes of comparing the two assays, the ADCC activity of effector cells was evaluated in parallel by both the $^{51}$chromium release assay and the anti-tumor cell proliferation assay. In these comparative assays, we used human effector cells isolated as described supra and suspended in RPMI-1640 supplemented with 5 mg/ml Gentamicin and 5–10% fetal calf serum. For a target cell we used GAGPA antibody labelled Zbtu tumor cells, at various effector cell to target cell ratios (E:T Ratio). The $^{51}$chromium assay was conducted (as described supra) for 4 hours and the anti-proliferation assay was conducted (as described supra) for 24 hours. The percentages of specific cytotoxicity as a measure of the $^{51}$chromium release assay and inhibition of tumor proliferation as a measure of the anti-tumor cell proliferation assay are shown in Table I.

TABLE I

| Assay # | Effector: Target Ratio | % Specific cytotoxicity | % Inhibition of proliferation |
|---|---|---|---|
| 1 | 100 | 51.7 | 107.4 |
|   | 50 | 38.5 | 89.4 |
|   | 25 | 30.4 | 59.2 |
|   | 12.5 | 28.1 | 33.3 |
|   | 6.25 | 18.4 | 25.0 |
| 2 | 100 | 73.7 | 99.7 |
|   | 50 | 39.1 | 99.8 |
|   | 25 | 29.6 | 91.9 |
|   | 12.5 | — | 55.7 |
|   | 6.25 | — | 34.9 |
| 3 | 100 | 61.5 | 84.2 |
|   | 50 | 53.0 | 69.4 |
|   | 25 | 41.2 | 46.1 |
|   | 12.5 | 18.6 | 32.3 |
|   | 6.5 | 6.7 | 24.0 |

$^{51}$Chromium release assay in vitro analyses have shown that ADCC sensitivity decreases in the presence of antibodies that induce antigenic modulation. Certain monoclonal antibodies (antigen associated with leukemia cells) have been shown to induce antigenic modulation such as CALLA (J. Ritz et al., "Serotherapy of Acute Lymphoblastic Leukemia with Monoclonal Antibodies", *Blood*, 58, pp. 141–52 (1981) and J. M. Pesando et al., "Distribution and Modulation of a Human Leukemia-Associated Antigen (CALLA)", *J. Immunology*, 131, pp. 2038–45 (1983)). As described below, the anti-proliferation assay was sensitive enough to detect an ADCC mediated effect when directed toward stable and modulating antigens. The assay was conducted in flasks undergoing either a gentle rocking motion or no rocking motion. The rocking motion provides cellular movement to facilitate cell to cell contact and possibly minimize the effect of antigenic modulation. The assays were performed as described supra, except that rocking was accomplished by placing the flasks on a rocker platform (LABQUAKE Labindustries, Berkeley, Calif. and set for approximately 40–50 rocking motions per minute. The tumor target cells were the Zbtu and Nalm-6 lines. The antibodies used included GAGPA, RaNalm or antiCALLA (#7500, Becton-Dickinson, Mountain View, Calif.). The results of both the anti-proliferation assay and the $^{51}$chromium release assay are shown in Table II.

TABLE II

| Target | Antibody | % Specific cytotoxicity | % Inhibition rocked | % Inhibition not-rocked |
| --- | --- | --- | --- | --- |
| Zbtu | none | 6.1 | 0 | 0 |
|  | GAGPA | 79.5 | 86.5 | 88.1 |
| Nalm-6 | none | 3.4 | 0 | 0 |
|  | RaNalm | 58.9 | 103.5 | 93.8 |
|  | CALLA | 7.1 | 47.3 | 10.9 |

Frozen Storage

We also employed these assays to evaluate the effect of frozen storage ($-75°$ C.) on effector cell ADCC activity by $^{51}$chromium release assays. The Zbtu tumor with GAGPA antibody was the target cell. Effector cells were obtained from three healthy donors as described supra and frozen according to the technique in Pross et al., "The Standardization of NK Cell Assays for Use in Studies of Biological Response Modifiers", *J. Immunological Methods*, 68, pp. 235–49 (1984). The cells were thawed after 12–58 days and washed two additional times in standard wash medium as described supra. The thawed effector cells were then activated as described supra. Table III demonstrates cell viability before and after freezing, the ADCC activity as expressed by percent cytotoxicity and percent recovery of viable cells after freezing.

TABLE III

| Donor | % Viability Day 0 | % Viability Day (X) | % Cytotoxicity Day 0 | % Cytotoxicity Day (X) | % Viable Cells Recovered |
| --- | --- | --- | --- | --- | --- |
| 1 | 94 | 93 (12) | 76 | 68 (12) | 67 |
| 2 | 92 | 80 (34) | 71 | 49 (34) | 58 |
| 3 | 97 | 94 (58) | 71 | 58 (58) | 62 |

Tumor Treated

The animal tumor treated in vivo according to the processes of this invention in the following examples was Zbtu, a T-cell leukemia/lymphoma originated in C3Hf inbred mice by intrathymic injection of the Gross passage A virus. Primary thymomas were excised, cells were suspended in sterile saline and injected intraperitoneally into normal adult C3Hf recipient mice to induce an ascites-form tumor. This tumor has been serially transferred in vivo since 1970. It has an $LD_{100}$ of less than 10 cells in C3Hf mice with an approximate mean survival time of 16 days. A subline of this tumor has been adapted for growth in vitro as well with no apparent loss of tumorigenicity. Zbtu tumor cells express the following surface antigens, detected by means of indirect immunofluorescence, complement dependent serum toxicity, FACS (fluorescence activated cell sorter) analysis and ADCC:

(1) Thy 1.2
(2) gP70
(3) p12
(4) Gross passage A virus

Antibodies used in the in vivo treatment of mice according to the processes of this invention were GAGPA antibodies.

EXAMPLE 1

C3Hf strain inbred mice (bred at University of Minnesota Mouse Colony and available from Microbiological Associates, Walkersville, Md.) were alloprimed three times, on days 0, 7, and 14, by transplanting a 5×5 mm section of whole spleen tissue from a C57B1/6J (Jackson Laboratories, Bar Harbor, Me.) strain donor subcutaneously into the ear capsule. On day 17, host spleens were aseptically excised from both the alloprimed mice and normal age matched controls. Spleen cells were harvested into Complete Dulbecco's Minimal Essential Medium (Gibco Laboratories, Grand Island, N.Y.) supplemented with 5% fetal calf serum, by passage through a stainless mesh screen, type 304, no. cx-30 (Small Parts Inc., Miami, Fla.). The spleen cells were cultured in one-way mixed lymphocyte cultures ("MLC") [J. C. Cerottini et al., "Generation Of Cytotoxic T-Lymphocytes In Vitro I. Response of Normal And Immune Mouse Spleen Cells In Mixed Leukocyte Culture", *J. Exp. Med.*, 140, p. 703 (1974)] for 3 to 7 days with C57B1/6J stimulator cells at a concentration of $1.0 \times 10^7$ cells/ml for both responders and stimulators at a 1:1 ratio. Responder cells were used as effector cells in a $^{51}$chromium release assay (as described supra) against GAGPA antibody labelled Zbtu tumor targets (Table IV).

Responder cells were also used as effector cells for in vivo treatment of mice bearing greater than $1 \times 10^5$ Zbtu leukemia cells. A balanced saline solution containing $1.0 \times 10^7$ effector cells and, in some cases, GAGPA antibody, was administered intravenously to leukemic C3Hf mice (Table V). In Table V, the Group A mice represented 10 mice, which had each received an intravenous injection of 0.1 ml GAGPA and 0.2 ml balanced saline solution. Group B mice represented 10 mice, which had each received an intravenous injection of 0.1 ml normal goat serum and 0.2 ml ($1.0 \times 10^7$ viable cells) effector cells in balanced saline solution. Group C mice represented 10 mice, which had each received an intravenous injection of 0.1 ml GAGPA and 0.2 ml ($1.0 \times 10^7$) effector cells in balanced saline solution.

TABLE IV

| Percent Specific ADCC - Day 5 MLC | | |
| --- | --- | --- |
| Effector:Target Ratio | Unprimed | Primed |
| 140:1 | 19.9 | 56.0 |
| 47:1 | 10.4 | 47.0 |
| 16:1 | 8.3 | 31.2 |

TABLE V

| Percent Survival of Treated Tumor-Bearing Mice | | | |
| --- | --- | --- | --- |
| Group | 6 weeks | 10 weeks | 18 weeks |
| A | 20 | 0 | 0 |
| B | 10 | 0 | 0 |
| C | 100 | 90 | 40 |

EXAMPLE 2

We isolated effector cells from peripheral blood of healthy human donors as follows. One unit (450 cc) of whole peripheral blood was drawn from a donor by venipuncture into a CPDA blood bag containing 63 ml anticoagulant-citrate phosphate-dextrose adenine-1 solution and placed in ten 50 ml tubes. The blood sample was then centrifuged in a Beckman TJ-6 centrifuge equipped with a TH-4 rotor for 10 min at 1200 rpm. As a result of the centrifugation, the red cells pelletized and the leukocytes formed a buffy coat which was harvested by pipetting through the top layer of plasma.

We collected the buffy coats from each tube and pooled them in a 50 ml tube before density centrifugation to further sort out effector cells. We then added Hank's balanced salt solution to a volume of 17.3 ml and carefully layered the volume onto 14 ml Ficoll-hypaque in a 50 ml glass tube. The tube was centrifuged in a Beckman TJ-6 centrifuge equipped with a TH-4 rotor for 30 min at 1400 rpm and at a temperature of 20° C. We removed and discarded the top layer using a pipette and collected the interface into a 50 ml glass tube and added 30 ml sterile wash medium (RPMI-1640 supplemented with at least 2% autologous serum). The tube was centrifuged for 15 min at 1400 rpm. We removed the supernatant and resuspended the effector cells in 8-10 ml wash medium. We then removed a small amount of the suspension to a microtube to count 1:100. Subsequently, we removed desired volumes of effector cells and washed them twice in wash medium or experimental medium. The leukocytes were suspended in RPMI 1640 culture medium at a concentration of $1 \times 10^7$ cells/ml.

We then cultured the leukocytes in a one-way mixed lymphocyte culture, prepared according to the method described supra, in a 1:1 ratio with either allogeneic (pooled from non-related donors) or xenogeneic (pooled from C57B1/6J inbred mouse spleens) stimulator cells which had been irradiated to 2500R. Responder cells were used as effector cells in a $^{51}$chromium release ADCC assay against unlabelled or GAGPA antibody-labelled Zbtu tumor targets before being mixed with the stimulator cells (day 0) and after remaining in culture with the stimulator cells for between 3 and 7 days. Table VI indicates the increase in ADCC activity, as measured in a $^{51}$chromium release assay (effector:target ratio=140:1) of effector cells treated with the mixed lymphocyte culture.

TABLE VI

| Stimulator | % Specific ADCC | | | |
|---|---|---|---|---|
| | Day 0 | Day 3 | Day 5 | Day 7 |
| Allogeneic | 38.1 | 61.5 | 86.2 | 79.5 |
| Xenogeneic | 38.1 | 53.2 | 66.6 | 59.7 |

EXAMPLE 3

We obtained 450 ml peripheral blood from healthy human donors according to the procedure set forth in Example 2, except that the blood was placed into two 250 ml bottles instead of ten 50 ml tubes and the leukocyte-containing buffy coats were not pooled. We resuspended the leukocytes in RPMI-1640 culture medium, containing Gentamicin (5 µg/ml), at a concentration of $1 \times 10^7$ cells/ml in the presence of varying amounts of gamma interferon (Cellular Products, Buffalo, N.Y.). The gamma interferon was present in amounts ranging between 100 and 1000 units per ml. The cultures obtained were maintained for between 1 and 4 days at either 4° C. in air or 37° C. in a 5% $CO_2$ atmosphere incubator. The treated effector cells were used in a $^{51}$chromium release ADCC assay against unlabelled or GAGPA antibody Zbtu labelled tumor targets before being mixed with the interferon and after each interferon treatment over the 1-4 day treatment period. Table VII indicates the increase in ADCC activity of the treated effector cells, as measured in the $^{51}$chromium release assay (effector:target ratio=140:1).

TABLE VII

| Units IFN | % Specific ADCC | | | | | | |
|---|---|---|---|---|---|---|---|
| | | 4° C. | | | 37° C. | | |
| | Day 0 | Day 1 | Day 2 | Day 4 | Day 1 | Day 2 | Day 4 |
| 100 | 36.3 | 39.1 | 43.7 | 45.9 | 42.8 | 46.6 | 39.1 |
| 200 | 36.3 | ND | ND | ND | 49.7 | 51.9 | 59.3 |
| 600 | 36.3 | 43.8 | 51.1 | 49.6 | 36.4 | 53.6 | 51.2 |
| 1000 | 36.3 | 33.2 | 36.1 | 39.4 | ND | ND | ND |

% specific ADCC are mean values
ND = Not determined.

EXAMPLE 4

We isolated human leukocyte effector cells and suspended them in RPMI-1640 culture medium, containing Gentamicin (5 µg/ml), at a concentration of $1 \times 10^7$ cells/ml as in Example 3. We added recombinant interleukin-2 (Genzyme Corporation, Boston, Mass.) to effector cell cultures in amounts ranging between 30 and 750 units per ml.

The cultures thus obtained were maintained for between 1 and 4 days at either 4° C. in air or 37° C. in a 5% $CO_2$ atmosphere incubator. The treated effector cells were used in a $^{51}$chromium release ADCC assay against unlabelled or GAGPA antibody labelled Zbtu tumor targets both before being mixed with the interleukin-2 and after each interleukin-2 treatment over the 1-4 day treatment period. Table VIII indicates the increase in ADCC activity of the treated effector cells, as measured in the $^{51}$chromium release assay (effector:target ratio=140:1).

TABLE VIII

| Units IL-2 | % Specific ADCC | | | | | | |
|---|---|---|---|---|---|---|---|
| | | 4° C. | | | 37° C. | | |
| | Day 0 | Day 1 | Day 2 | Day 4 | Day 1 | Day 2 | Day 4 |
| 30 | 43.2 | 36.9 | 46.3 | 51.2 | 51.6 | 62.3 | 55.4 |
| 50 | 43.2 | ND | ND | ND | 39.5 | 51.9 | 60.7 |
| 100 | 43.2 | 48.7 | 49.6 | 54.6 | ND | ND | ND |
| 250 | 43.2 | 39.2 | 55.4 | 49.3 | 56.4 | 62.1 | 57.8 |
| 500 | 43.2 | ND | ND | ND | 60.6 | 63.7 | 59.4 |
| 750 | 43.2 | 36.1 | 52.7 | 61.1 | 61.4 | 60.9 | 58.3 |

% specific ADCC are mean values
ND = Not determined.

EXAMPLE 5

Human leukocyte effector cells were isolated and suspended in RPMI-1640 culture medium, containing Gentamicin (5 µg/ml), at a concentration of $1 \times 10^7$ cells/ml as in Example 4. We then added gamma interferon (Cellular Products, Buffalo, N.Y.) to the cultures in amounts varying between 100-1000 units/ml and maintained the cultures for between 1 and 4 days at 37° C. in a 5% $CO_2$ atmosphere incubator. The effector cells were then washed three times in RPMI-1640 culture medium to remove the added interferon. We then added interleukin-2 (Genzyme Corporation, Boston, Mass.) to the cells in amounts varying between 100–600 units/ml, and maintained the cells for between 1 and 4 days at 37° C. in a 5% $CO_2$ atmosphere incubator. The effector cells were then used in a $^{51}$chromium release ADCC assay against unlabelled targets of Zbtu tumors and of Nalm-6 tumors, GAGPA antibody-labelled Zbtu tumor targets and rabbit anti-Nalm-6 labelled Nalm-6 tumor targets before being mixed with the lymphokines and after each lymphokine treatment over the treatment period and the percent ADCC activity was determined.

Table IX depicts the increase in ADCC activity of the treated effector cells (effector:target ratio=140:1).

TABLE IX

| | % Specific ADCC | | | | |
|---|---|---|---|---|---|
| | GAGPA-labelled Zbtu targets | | | Rabbit anti-Nalm-6 labelled Nalm-6 targets | |
| Group | Day 0 | Day 2 | Day 4 | Day 6 | Day 0 | Day 4 |
| A | 41.4 | 66.7 | 89.1 | 76.3 | 36.3 | 75.2 |
| B | 41.4 | ND | 79.8 | 73.6 | 36.3 | 88.7 |
| C | 41.4 | 90.1 | 106.5 | 101.3 | 36.3 | 94.3 |
| D | 41.4 | 88.2 | 91.4 | ND | 36.3 | ND |
| E | 41.4 | 75.5 | 86.3 | 89.1 | 36.3 | ND |

A - 600 units IFN, 500 units IL-2
B - 600 units IFN, 250 units IL-2
C - 200 units IFN, 600 units IL-2
D - 600 units IFN, 600 units IL-2
E - 1000 units IFN, 100 units IL-2
For all groups, effector cells were cultured for equal time duration in IFN (first) and IL-2 (second).
ND - not determined.

EXAMPLE 6

We isolated human leukocyte effector cells as in Example 5 and suspended them in RPMI-1640 with 5% autologous serum at a concentration of $1 \times 10^7$ cells/ml. We then measured % ADCC of these cells in a $^{51}$chromium release ADCC assay.

Subsequently, we washed the effector cells three times in RPMI-1640 medium to remove the autologous serum and suspended them in RPMI 1640 culture medium, containing Gentamicin (5 μg/ml), and which was supplemented with either 1% ULTROSER G, 5% autologous serum, 5% fetal calf serum or 5% pooled allogenic serum. We maintained the cultures for between 1 and 4 days at either 4° C. in air or 37° C. in a 5% $CO_2$ atmosphere. The effector cells were used in a $^{51}$chromium release ADCC assay against unlabelled targets of Zbtu tumors and of Nalm-6 tumors, GAGPA antibody labelled Zbtu tumor targets, Anti-CALLA labelled Nalm-6 targets and rabbit anti-Nalm-6 labelled Nalm-6 tumors, before being mixed with any RPMI-1640 supplemented medium and after each treatment period and the percent ADCC activity was determined.

Table X depicts the increase in ADCC activity of the treated effector cells (effector:target ratio=140:1) against GAGPA antibody labelled Zbtu tumor targets. Table XI depicts the increase in ADCC activity of treated effector cells (effector:target ratio=140:1) against Nalm-6 tumor targets labelled with either Anti-CALLA or rabbit anti-Nalm-6 antibodies.

TABLE X

| | % Specific ADCC | | | | | |
|---|---|---|---|---|---|---|
| Culture Medium | 4° C. | | | 37° C. | | |
| | Day 0 | Day 1 | Day 2 | Day 4 | Day 1 | Day 2 | Day 4 |
| A | 38.6 | 39.6 | 41.3 | 38.6 | 39.3 | 40.2 | 42.8 |
| B | 38.6 | 43.1 | 36.3 | 31.8 | 41.4 | 33.2 | 36.8 |
| C | 38.6 | 68.7 | 83.2 | 79.4 | 81.5 | 93.1 | 86.4 |
| D | 38.6 | 64.4 | 69.7 | 91.5 | 86.7 | 78.5 | 85.3 |

TABLE XI

| | % Specific ADCC | | | |
|---|---|---|---|---|
| Culture Medium | Anti-CALLA labelled Nalm-6 targets (37° C.) | | Rabbit anti-Nalm-6 labelled Nalm-6 targets (37° C.) | |
| | Day 0 | Day 2 | Day 0 | Day 2 |
| A | 12.1 | 17.3 | 32.1 | 31.1 |
| B | 12.1 | 13.4 | 32.1 | 39.5 |
| C | 12.1 | 37.8 | 32.1 | 69.4 |
| D | 12.1 | 39.1 | 32.1 | 61.6 |

A - RPMI-1640 supplemented with 1% Ultroser G (LBK Industries, Gaithersburg, Maryland)
B - RPMI-1640 supplemented with 5% autologous serum
C - RPMI-1640 supplemented with heat inactivated 5% fetal calf serum (Gibco Laboratories, Grand Island, New York)
D - RPMI-1640 supplemented with 5% pooled allogenic serum

EXAMPLE 7

We isolated human effector cells as described in Example 6 and suspended them in either RPMI-1640, containing Gentamycin (5 μg/ml), and supplemented with 5% autologous serum or 1% ULTROSER G (non-activated cells) or RPMI-1640 supplemented with 5% fetal calf serum (activated cells), to attain a cell concentration in each suspension of $1 \times 10^7$ cells/ml. We measured the percent anti-proliferation activity by ADCC of the treated effector cells against Zbtu target cells, labelled with GAGPA antibodies and Nalm-6 target cells, labelled with rabbit anti-Nalm-6 antibodies after a 1 or 2 day treatment period.

Table XII demonstrates the inhibition of proliferation of target tumor cells by the treated effector cells.

TABLE XII

| | % Anti-Proliferation | | | |
|---|---|---|---|---|
| | Zbtu targets | | Nalm-6 targets | |
| Effector | Day 1 | Day 2 | Day 1 | Day 2 |
| Non-activated | 24.3 | 32.1 | 20.1 | 19.6 |
| Activated | 84.2 | 78.8 | 82.6 | 92.3 |

EXAMPLE 8

The use of monoclonal antibodies to attach and thereby "arm" an effector cell was evaluated in both the $^{51}$chromium release assay and the anti-proliferation assay. Monoclonal antibodies capable of recognizing antigens expressed on the Zbtu cell surface were analyzed for their ability to mediate ADCC. The IgG2a class monoclonal antibody anti-Thy 1.2 (#630021, Miles Scientific) and the IgG2b class monoclonal antibody anti-Thy 1.2 (#1330, Becton-Dickinson, Mountain View, Calif.) recognize the Thy 1.2 antigen expressed on murine "T" cells and the Zbtu tumor cell line. The assays used Zbtu target cells unlabelled or labelled with GAGPA as a control. The human effector cells were either "unarmed" (not manipulated) or armed with antibody (GAGPA or Thy 1.2). The results of these assays are shown in Table XIII.

TABLE XIII

| Target cell | Antibody | Effector | % Specific cytotoxicity | % Inhibition proliferation |
|---|---|---|---|---|
| Zbtu | None | unarmed | 5.9 | 0 |
| Zbtu | GAGPA | unarmed | 79.1 | 86.6 |
| Zbtu | GAGPA | armed | 65.3 | 79.7 |
| Zbtu | THY 1.2(2a) | unarmed | 78.6 | 104.5 |
| Zbtu | THY 1.2(2a) | armed | 74.3 | 88.8 |
| Zbtu | THY 1.2(2b) | unarmed | 82.5 | 86.3 |
| Zbtu | THY 1.2(2b) | armed | 75.4 | 89.8 |

EXAMPLE 9

We obtained leukocytes from the peripheral blood of each of eight human donors diagnosed with leukemia by drawing 50 ml of blood into a 60 ml syringe containing 2 ml of heparin (heparin sodium injection-1000 USP units/ml, Elkins-Sinn, Inc., Cherry Hill, N.J.) anticoagulant. The leukocytes were subsequently isolated as described in Example 2. Effector cells were analyzed by $^{51}$chromium release ADCC assay against unlabelled and GAGPA antibody-labelled Zbtu tumor targets and autologous tumor targets without further manipulation as controls.

Cultured effector cells were stimulated with 10% allogeneic or 10% xenogeneic serum, containing Gentamycin (5 μg/ml), at a concentration of $1 \times 10^7$ cells/ml for 1 to 5 days and re-assayed for ADCC. Table XIV demonstrates the ability of leukemia donors' effector cells to mediate ADCC against various Zbtu tumor target cells and autologous tumor target cells.

TABLE XIV

| | | | % Specific ADCC | | | |
|---|---|---|---|---|---|---|
| Pa- | | | Zbtu targets | | Autologous tumor targets | |
| tient # | Diag- nosis | Treat- ment | Sta- tus | Day 0 | Day 2 | Day 0 | Day 2 |
| 1 | ALL | CC | Acute | 32.6 | 58.4 | 31.1 | 53.4 |
| 2 | CML | CC | Re-lapse | 14.0 | 21.1 | 13.3 | 37.7 |
| 3 | CLL | CC | Rem | 49.5 | 83.4 | ND | ND |
| 4 | ALL | CC | Rem | 19.8 | 62.7 | ND | ND |
| 5 | CLL | CC | Re-lapse | 8.7 | 12.2 | 5.4 | 18.7 |
| 6 | CML | BMT | Rem | 31.4 | 60.9 | ND | ND |
| 7 | T lymph | CC | Rem | 23.2 | 71.1 | ND | ND |
| 8 | CLL | CC | Rem | 45.1 | 52.4 | ND | ND |

Definitions:
ALL - acute lymphocytic leukemia
CLL - chronic lymphocytic leukemia
CML - chronic myelogenous leukemia
T lymph - "T" cell lymphoma
CC - combined chemotherapy
BMT - bone marrow transplant (allogeneic)
Rem - remission
ND - not determined.

Patients 2 and 5 in Table XIV had extensive contamination of tumor cells in the peripheral blood specimen. In both patients, greater than 80% of the effector cells were malignant. Therefore, the adjusted concentration of effector cells in each of these patient's blood samples was equivalent to approximately 20% of recovery of the concentration of effector cells in blood samples obtained from the other patients. In addition, patients 3, 4, 6, 7 and 8, who were in remission at the time of treatment, did not have any circulating tumor cells in their peripheral blood.

EXAMPLE 10

We obtained leukocytes from the peripheral blood of each of four human patients diagnosed with leukemia. Blood was drawn and leukocytes isolated as described in Example 8. The leukocytes were cultured for 24 hours at 37° C. in a humidified $CO_2$ (10%) incubator in RPMI-1640 supplemented with 10% fetal calf serum. The effector cells were analyzed by $^{51}$chromium release ADCC assay against the Zbtu tumor target cells unlabelled or labelled with either GAGPA polyclonal antibody, Thy 1.2-2a or Thy 1.2-2b monoclonal antibodies. The results are listed in Table XV.

TABLE XV

| Pa- tient # | Diag- nosis | Treat- ment | Sta- tus | None | Antibody GAGPA | THY 1.2: (2a) | (2b) |
|---|---|---|---|---|---|---|---|
| 1 | CML | CC | Rem | 0 | 16 | 39 | 13 |
| 2 | ALL | CC | Rem | 0 | 68 | 71 | 64 |
| 3 | CML | None | Chronic | 1 | 22 | 45 | 16 |
| 4 | CML | None | Chronic | 1 | 39 | 65 | 23 |

EXAMPLE 11

We obtained leukocytes from the peripheral blood of each of five human patients diagnosed with leukemia. The blood was drawn and leukocytes isolated as described in Example 8. The effector cells were treated by one of five procedures: (1) unmanipulated; (2) cultured for 48 hours in RPMI-1640 supplemented with 10% fetal calf serum (3) cultured for 48 hours in RPMI-1640 supplemented with IL-2 (70 units/ml); (4) cultured for 48 hours in RPMI-1640 supplemented with IFN (300 units/ml); (5) cultured sequentially, first for 24 hours in RPMI-1640 supplemented with IFN (300 units/ml), washed two times in standard wash medium (as described supra), and cultured for an additional 24 hours in IL-2 (70 units/ml). All cultures were incubated in a humidified $CO_2$ (10%) incubator at 37° C. The effector cells were analyzed by $^{51}$chromium release ADCC assay against Zbtu tumor target cells labelled with GAGPA polyclonal antibody. The results are listed in Table XVI.

TABLE XVI

| Pa- tient # | Diag- nosis | Treat- ment | Sta- tus | Day 0 | FCS | IL-2 | IFN | IFN/ IL-2 |
|---|---|---|---|---|---|---|---|---|
| 1 | ALL | None | Acute | 23 | — | — | 30 | 31 |
| 2 | CML | None | Chron-ic | 39 | 45 | 45 | — | — |
| 3 | CML | CC | Rem | 16 | 40 | 28 | — | — |
| 4 | CML | CC | Re-lapse | 12 | 33 | 20 | — | 21 |
| 5 | CML | None | Chron-ic | 22 | 51 | — | — | — |

EXAMPLE 12

We analyzed effector cells which had been activated according to the process of this invention by flow cytometry for binding of monoclonal antibodies bodies Leu-11a by direct immunofluorescence and Leu-11b by indirect immunofluorescence. Leu-11a and Leu-11b are antibodies which are believed to recognize the Fc receptor on large granular lymphocytes and granulocytes (B. Perussia et al., "The Fc Receptor for IgG On Human Natural Killer Cells: Phenotypic, Functional And Comparative Studies Using Monoclonal Antibodies", *J. Immunol.*, 133, p. 180 (1984)).

We isolated human leukocyte effector cells as in Example 5 and treated the cells with either autologous serum or fetal calf serum, γ-IFN, IL-2 or a γ-IFN+IL-2 mixture according to the procedures set forth in, respectively, examples 7, 3, 4 and 5. The specific times and temperatures of treatment, as well as the concentrations of serum or lymphokine used are set forth in Table XVII.

We took cells from each treatment group and suspended them in phosphate buffered saline (PBS, 0.01M phosphate, 0.15M NaCl, pH 7.2–7.4) at a concentration of $1 \times 10^6$ viable cells/ml and washed the cells by centrifugation in a Beckman TJ-6 centrifuge equipped with a TH-4 rotor for 5 min at 1200 rpm. We divided the cell pellets into four groups and resuspended each group in one of the following:

Group A: Leu-11a, 5 μl antibody, 40 μl PBS, to achieve a 1:9 dilution

Group B: Mouse IgG1, 6 μl of 200 μg/ml concentration for $1 \times 10^6$, cells [non-specific control]

Group C: Leu-11b, 5 μl antibody, 40 μl PBS, to achieve a 1:9 dilution

Group D: MOPC 104E purified mouse myeloma protein, 5 μl of a 1:5 dilution per $1 \times 10^6$ cells [non-specific control].

Each of the four groups of cells were incubated for 30 min at 4° C. in a container which was covered from ambient light. We then washed the effector cells twice, each time adding 1.0 ml PBS and centrifuging the mixture for 5 min at 1200 rpm.

The cells of each of Group A and Group B were then resuspended in 1.0 ml PBS to a concentration of $1.0 \times 10^6$ viable cells/ml and analyzed.

The cells of each of Group C and Group D were resuspended in affinity purified fluorescein isothiocyanate (FITC) conjugated goat anti-mouse IgM antibody (Tago, Inc., Burlingame, Calif.) by adding 0.10 ml of a 1:50 antibody dilution in PBS. These effector cells were then incubated for an additional 30 min at 4° C. in a container covered from the light. We washed each group of cells twice, each time adding 1.0 ml PBS and centrifuging the mixture for 5 min at 1200 rpm. The cells of each group were then re-suspended in 1.0 ml PBS to a concentration of $1.0 \times 10^6$ viable cells/ml and analyzed.

The effector cells were then evaluated for immunofluorescence by flow cytometry analysis in a FACS® IV cell sorter both before being treated with the serum or lymphokines and after serum or lymphokine treatment and exposure to the antibodies. FITC was excited by using 400 mW of 488 nM light (argon laser). Fluorescence emission was collected by a 90° angle focusing lens. Green light passed through a 530 nM band pass filter into a photomultiplier tube (EMI No. 99224 A). Green fluorescence 90° angle light scatter peak amplitudes of electrical signals were converted from analog to digital, amplified by a linear amplifier and assigned into 256 channels. Histograms were plotted with the fluorescence channels on the X-axis and the relative number of positive cells on the Y-axis. Non-specific control values (Groups B and D) were subtracted from the experimental values to obtain mean channel values and % positive cells (Mean Channel Experimental—Mean Channel Control=Mean Channel Difference, and % positive cells). The % positive cell data reflects the number of cells which specifically bound antibody. The mean channel data indicates the intensity of immunofluorescence on the positive cells and, thus, the relative quantity of antibody binding which occurred.

The effector cells were also used in a $^{51}$chromium release ADCC assay (effector:target ratio=140:1) against GAGPA antibody-labelled Zbtu tumor targets both before being treated with the serum or lymphokines and after those treatments and exposure to the antibodies.

TABLE XVII

| Effector | Day 0 Mean Channel Difference | Day 0 % Positive Cells | Day 0 % ADCC | Day 1 Mean Channel Difference | Day 1 % Positive Cells | Day 1 % ADCC | Day 2 Mean Channel Difference | Day 2 % Positive Cells | Day 2 % ADCC |
|---|---|---|---|---|---|---|---|---|---|
| Control (4° C.) | 62.2 | 16.9 | 26.4 | 64.2 | 18.1 | 22.8 | 60.6 | 17.2 | ND |
| Control (37° C.) | 58.6 | 18.1 | 31.4 | 52.9 | 21.9 | 27.5 | 56.9 | 20.7 | 30.7 |
| FCS (37° C.) | ND | ND | ND | 77.6 | 34.9 | 59.8 | 91.1 | 31.6 | 56.3 |
| IFN (37° C.) | ND | ND | ND | 76.8 | 24.2 | 49.1 | 77.2 | 26.3 | ND |
| IL-2 (37° C.) | ND | ND | ND | 88.2 | 20.4 | 52.6 | 110.2 | 24.4 | 61.5 |
| IFN + IL-2 (37° C.) | ND | ND | ND | 85.0 | 37.7 | 61.4 | 73.8 | 34.8 | 60.9 |

Control - RPMI-1640 supplemented with 5% autologous serum
FCS - RPMI-1640 supplemented with 5% heat inactivated fetal calf serum
IFN - RPMI-1640 containing 600 units γ-IFN/$10^6$ cells
IL-2 - RPMI-1640 containing 500 units IL-2/$10^6$ cells
IFN + IL-2 - RPMI-1640 containing 200 units γ-IFN + 600 units IL-2/$10^6$ cells
ND - Not determined Having described our invention with particular reference to the preferred form thereof, it will be apparent to those skilled in the art to which the invention pertains that various changes and modifications may be made therein without departing from the spirit and scope of the invention as defined by the claims appended hereto.

We claim:

1. A process for increasing the antibody dependent cell-mediated cytotoxicity (ADCC) of leukocyte effector cells that express or have the potential to express Fc receptors for antibody comprising:

a) activating the effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated; and b) contacting the activated effector cells with a target cell that is susceptible to ADCC in the presence of an antibody which is capable of ADCC mediation and which primarily immunoreacts with an antigen that is specific to the target cell or that is present in higher densities on the target cell than on normal cells.

2. A process for increasing the antibody dependent cell-mediated cytotoxicity (ADCC) of leukocyte effector cells comprising:
 a) selectively isolating leukocytes that express or have the potential to express Fc receptors for antibody;
 b) activating the effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated; and
 c) contacting the activated effector cells with a target cell that is susceptible to ADCC in the presence of an antibody which is capable of ADCC mediation and which primarily immunoreacts with an antigen that is specific to the target cell or that is present in higher densities on the target cell than on normal cells.

3. The process of claim 2 wherein the effector cells are selectively isolated by obtaining cells having a diameter in the size range from 7 μm to 25 μm.

4. The process of claim 2 further comprising labeling said effector cells with a monoclonal antibody and isolating said effector cells by positive selection.

5. A method of obtaining and using leukocyte effector cells that express or have the potential to express Fc receptors for antibody in effective target cell killing quantities comprising:
 a) selectively isolating leukocytes that express or have the potential to express Fc receptors for antibody;
 b) activating the effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated;
 c) proliferating the activated effector cells using in vitro tissue culture reproduction methods; and
 d) contacting the proliferating effector cells with ADCC susceptible target cells in the presence of an antibody which is capable of ADCC mediation and which primarily immunoreacts with an antigen that is specific to the target cell or that is present in higher densities on the target cell than on normal cells.

6. A method of obtaining leukocyte effector cells that express or have the potential to express Fc receptors for antibody in effective target cell killing quantities comprising:
 a) selectively isolating leukocytes that express or have the potential to express Fc receptors for antibody;
 b) proliferating the effector cells using in vitro tissue culture reproduction methods; and
 c) activating the proliferated effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated.

7. A method for preserving, reviving, and using ADCC mediating effector cells comprising:
 a) obtaining an effective target cell killing quantity of leukocyte effector cells that express or have the potential to express Fc receptors for antibody;
 b) activating the effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated;
 c) freezing the effector cells to store them in indefinite periods of time;
 d) thawing the effector cells; and
 e) contacting the activated effector cells with ADCC susceptible target cells in the presence of an antibody which is capable of ADCC mediation and which primarily immunoreacts with an antigen that is specific to the target cell or that is present on the target cell in higher densities than on normal cells.

8. A method for preserving, reviving, and using ADCC mediating effector cells comprising:
 a) obtaining an effective target cell killing quantity of leukocyte effector cells that express or have the potential to express Fc receptors for antibody;
 b) freezing the effector cells to store them for indefinite periods of time;
 c) thawing the effector cells;
 d) activating the effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated; and
 e) contacting the activated effector cells with ADCC susceptible target cells in the presence of an antibody which is capable of ADCC mediation and which primarily immunoreacts with an antigen that is specific to the target cell or that is present on the target cell in higher densities than on normal cells.

9. A composition for use in the killing of disease target cells consisting essentially of:
 a) a quantity of leukocyte effector cells that express Fc receptors for antibody, and that have been activated by combining them in vitro with gamma interferon and interleukin-2, simultaneously or sequentially, or with gamma interferon alone for a sufficient period of time to increase the ADCC activity of said effector cells to at least 1.25 to 125 times that of effector cells that have not been activated; and
 b) a quantity of gamma interferon or a combination of gamma interferon and interleukin-2 sufficient for such activation;
 wherein said activated effector cells are capable of mediating ADCC against disease target cells in the presence of an antibody which primarily immunoreacts with an antigen that is specific to the disease target cell or that is present in higher densities on the disease target cell than on normal cells, so that such composition has cytotoxic effect specifically on disease target cells.

10. A composition for use in the killing of disease target cells comprising:
 a) a quantity of leukocyte effector cells that express or have the potential to express Fc receptors for antibody, and that have been activated by combining them in vitro, simultaneously or sequentially, with amounts of gamma interferon and interleukin-2 for sufficient period(s) of time to increase the ADCC activity of said quantity of effector cells to a level higher than that attained with said amount of interleukin-2 alone; and b) a monoclonal antibody which is capable of ADCC mediation and which primarily immunoreacts with an antigen that is specific to the disease target cell or that is present in higher densities on the disease target cell than on normal cells.

11. A composition for use in the killing of disease target cells comprising;

a) a quantity of leukocyte effector cells that express Fc receptors for antibody, and that have been activated by combining them in vitro, simultaneously or sequentially, with amounts of gamma interferon and interleukin-2 for sufficient period(s) of time to increase the ADCC activity of said quantity of effector cells to a level higher than that attained with said amount of interleukin-2 alone; and b) a polyclonal antibody preparation that is capable of ADCC mediation and which selectively immunoreacts with the disease target cell or with an antigen that is present in higher densities on the disease target cell than on normal cells, wherein such composition has cytotoxic effect specifically on such disease target cells.

12. A process for increasing the antibody dependent cell-mediated cytotoxicity (ADCC) of leukocyte effector cells that express or have the potential to express Fc receptors for antibody comprising:

a) activating the effector cells in vitro by combining them with gamma interferon and interleukin-2, simultaneously or sequentially, or with gamma interferon alone for a sufficient period of time to increase the ADCC activity of said effector cells to at least 1.25 to 125 times that of effector cells that have not been activated; and b) "arming" the activated effector cells in vitro with an antibody which is capable of ADCC mediation and which primarily immunoreacts with an antigen that is specific to a target cell that is susceptible to ADCC or that is present in higher densities on said target cell than on normal cells.

13. The method of claim 12 further comprising contacting the armed effector cells with the target cell which is susceptible to ADCC.

14. The process of claim 13 further comprising contacting the armed activated effector cells with the target cell in the presence of:

a) an additional amount of the antibody used for arming; or b) with an amount of a second antibody which is capable of ADCC mediation and which recognizes a second antigen that is specific to the target cell or that is present in higher densities on the target cell than on normal cells.

15. An effector cell activated by interleukin-2 and gamma interferon and armed with an antibody obtained according to the process of claim 12.

16. A process for increasing the antibody dependent cell-mediated cytotoxicity (ADCC) of leukocyte effector cells that express or have the potential to express Fc receptors for antibody comprising:

a) activating the effector cells in vitro by combining them in a Mixed Lymphocyte Culture (MLC) for a sufficient period of time to increase the ADCC activity of said effector cells to at least 1.25 to 125 times that of effector cells that have not been activated; and b) contacting the activated effector cells with a target cell that is susceptible to ADCC in the presence of an antibody which is capable of ADCC mediation and which primarily immunoreacts with an antigen that is specific to the target cell or that is present in higher densities on the target cell than on normal cells.

17. The process of claim 16 further comprising the step of arming the activated effector cells in vitro with an antibody before contacting the effector cells with the target cell.

18. A composition for use in the killing of disease target cells comprising:

a) a quantity of leukocyte effector cells that express Fc receptors for antibody, and that have been activated by combining them in vitro in a Mixed Lymphocyte Culture (MLC) for a sufficient period of time to increase the ADCC activity of said effector cells to at least 1.25 to 125 times that of effector cells that have not been activated; and b) a monoclonal antibody or a polyclonal antibody preparation which is capable of ADCC mediation and which primarily immunoreacts with an antigen that is specific to the disease target cell or that is present in higher densities on the disease target cell than on normal cells, so that such composition has cytotoxic effect specifically on disease target cells.

19. An antibody armed effector cell that is the product of an ADCC activating process comprising:

a) activating effector cells in vitro by combining them in a Mixed Lymphocyte Culture (MLC) for a sufficient period of time to increase the ADCC activity of said effector cells to at least 1.25 to 125 times that of effector cells that have not been activated; and b) arming the activated effector cells in vitro with an antibody which is capable of ADCC mediation and which primarily immunoreacts with an antigen that is specific to the target cell or that is present in higher densities on the target cell than on normal cells.

20. The process of claim 1, 2, 3, 4, 5, 7, 8, 12, 14, 16, 17 or 18 wherein the ADCC mediating antibody is a monoclonal antibody.

21. The process according to claim 2, 3, 4, 5, 7 or 8 wherein the effector cells are armed with the ADCC mediating antibody prior to contacting with said target cells.

* * * * *